(12) United States Patent
Loubens et al.

(10) Patent No.: US 6,689,096 B1
(45) Date of Patent: Feb. 10, 2004

(54) MULTIPURPOSE CATHETER

(75) Inventors: Thierry Loubens, Lyons (FR); Antoine Watrelot, Lyons (FR)

(73) Assignee: Soprane S.A., Lyons (FR)

( * ) Notice: Subject to any disclaimer, the term of this patent is extended or adjusted under 35 U.S.C. 154(b) by 0 days.

(21) Appl. No.: 09/529,415

(22) PCT Filed: Oct. 5, 1998

(86) PCT No.: PCT/FR98/02119

§ 371 (c)(1),
(2), (4) Date: Apr. 28, 2000

(87) PCT Pub. No.: WO99/22800

PCT Pub. Date: May 14, 1999

(30) Foreign Application Priority Data

Oct. 31, 1997 (FR) .............................................. 97 13988

(51) Int. Cl.$^7$ ........................ A61M 29/00; A61M 31/00; A61M 25/00; A61M 25/01; A61M 36/00
(52) U.S. Cl. ................................. 604/96.01; 604/97.02; 604/93.01; 604/533; 604/284; 600/7
(58) Field of Search ................................. 604/265, 177, 604/102.02, 27, 264, 523, 918, 96.01, 535, 103.1, 243, 533, 284, 285, 539; 600/505, 585, 7

(56) References Cited

U.S. PATENT DOCUMENTS

| | | | |
|---|---|---|---|
| 3,593,713 A | * 7/1971 | Bogoff et al. ........... | 604/102.02 |
| 4,670,009 A | 6/1987 | Bullock | |
| 5,046,503 A | * 9/1991 | Schneiderman ............. | 600/466 |
| 5,183,464 A | 2/1993 | Dubrul et al. | |
| 5,226,427 A | * 7/1993 | Buckberg et al. ............ | 600/585 |
| 5,344,397 A | * 9/1994 | Heaven et al. ............... | 604/920 |
| 5,431,676 A | 7/1995 | Dubrul et al. | |
| 5,437,637 A | 8/1995 | Lieber et al. | |
| 5,487,730 A | 1/1996 | Marcadis et al. | |
| 5,514,092 A | 5/1996 | Forman et al. | |
| 5,569,183 A | 10/1996 | Kieturakis | |
| 5,662,607 A | 9/1997 | Booth et al. | |
| 5,713,849 A | * 2/1998 | Bosma et al. ................. | 604/28 |
| 5,797,869 A | * 8/1998 | Martin et al. ............... | 604/177 |
| 5,908,403 A | * 6/1999 | Bosma et al. ................. | 604/43 |
| 6,206,870 B1 | * 3/2001 | Kanner ........................ | 604/523 |
| 6,306,074 B1 | * 10/2001 | Waksman et al. ............... | 600/7 |

FOREIGN PATENT DOCUMENTS

| | | |
|---|---|---|
| EP | 0277364 | 8/1988 |
| EP | 0495263 | 7/1992 |
| FR | 2607707 | 6/1988 |
| WO | 92/17236 | 10/1992 |
| WO | 97/37716 | 10/1997 |

* cited by examiner

Primary Examiner—Michael J. Hayes
Assistant Examiner—Roz Ghafoorian
(74) Attorney, Agent, or Firm—Greenblum & Bernstein, P.L.C.

(57) ABSTRACT

Multipurpose catheter including a small diameter cylindrical body including a first end, a second end, and at least three internal non-coaxial channels. A connection mechanism is disposed adjacent the first end for communicating with the non-coaxial channels. The connection mechanism comprises an ergonomic monobloc head which is sealingly attached to the first end of the cylindrical body. The monobloc head comprises a bulged wall having at least three independent inlets for communicating with the three non-coaxial channels via bores and two walls which continue from the bulged wall. An inwardly curved connecting wall is also included. The connecting wall is disposed adjacent the first end of the cylindrical body and connects the two walls. The two walls comprise first opposite facing inclined surfaces and second opposite facing inclined surfaces having a different inclination. One of the at least three channels is adapted to provide communication between at least one of the independent inlets and an elastically deformable balloon disposed adjacent the second end. Two of the at least three channels are adapted to allow the introduction of one of a liquid and a surgical mandrin. The ergonomic monobloc head is adapted to be gripped by a user.

34 Claims, 16 Drawing Sheets

MULTIPURPOSE CATHETER

BACKGROUND OF THE INVENTION

1. Field of the Invention

The present invention relates to a disposable multipurpose catheter making it possible in particular to introduce into the human body, at the operating site, surgical mandrins or to inject liquid such as serum or methylene blue in order to perform various pre-operative and intra-operative tests.

2. Description of Background and Relevant Information

Multipurpose catheter is understood as meaning a catheter/trocar having the function of a tool for perforating the walls and the function of a catheter for introducing, into the operating site, either liquid products or a range of surgical mandrins or other instruments, or both simultaneously.

Catheters of this type are known which comprise a cylindrical body integral at one of its ends with a head which is equipped with two access routes or inlets, while the other end is provided with a balloon which can deform elastically under the effect of a pressure.

This type of catheter makes it possible to perform certain tests or operations but it cannot simultaneously receive surgical mandrins and injection of liquids or passage of a miniature endoscope on account of the fact that the channels formed in the cylindrical body are coaxial to each other and centred in relation to the main axes of the body.

A first channel, centred about the main axes of the body, permits the insertion of a miniature endoscope or the passage of a liquid or the insertion of a surgical mandrin. All of its elements being introduced separately and independently. The second channel coaxial to the first one is provided solely to elastically deform the balloon.

U.S. Pat. No. 5,437,637 likewise discloses a catheter which comprises a flexible cylindrical body having, in its inner part, several non-coaxial channels for the passage of stiffening elements, instruments and/or liquids. This catheter comprises, on its outer periphery, a balloon which can dilate under the effect of a pressure.

It will be noted that, because of its flexibility, this type of catheter cannot be used as a trocar for perforating walls. Moreover, the connection means permit introduction, into each non-coaxial channel, either of instruments or liquids, but they do not allow the surgeon to hold the catheter in order to be able to use it as a tool.

It is these disadvantages which the present invention is intended to eliminate in particular.

SUMMARY OF THE INVENTION

The invention provides for a multipurpose catheter intended to permit various interventions, comprising a cylindrical body of small diameter which has, at one of its ends, a connection mechanism which communicates with non-coaxial channels formed in the inner part of the cylindrical body in such a way that at least one of the channels supplies, to the end remote from that bearing the connection mechanism a balloon which is able to deform elastically under the effect of a pressure, characterized in that the connection mechanism includes a monobloc head made of rigid plastic material which is injection-molded to attach itself in a sealed manner around the cylindrical body, while the head includes independent inlets which communicate with the non-coaxial channels via bores, so that the channels permit introduction either of liquids or of a range of surgical mandrins and/or other instruments, or both simultaneously at the different operating sites.

The invention also provides for a multipurpose catheter characterized in that the head consists of a slightly bulged wall receiving the independent inlets joining opposite the wall via another wall of inwardly curved profile in such a way that the head has an ergonomic profile facilitating the gripping of the catheter.

The invention also provides for a multipurpose catheter characterized in that each wall has surfaces of different inclinations.

The invention also provides for a multipurpose catheter intended to permit various interventions, comprising a cylindrical body of small diameter which has, at one of its ends, connection mechanism which communicates with non-coaxial channels formed in the inner part of the cylindrical body in such a way that at least one of the channels supplies, to the end remote from that bearing the connection mechanism, a balloon which is able to deform elastically under the effect of a pressure, characterized in that the cylindrical body has, remote from the connection mechanism, an end with a conical profile.

The invention also provides for a multipurpose catheter characterized in that the conical profile of the end of the cylindrical body has its axis on the main channel.

The invention also provides for a multipurpose catheter characterized in that the main channel is eccentric in relation to the external diameter of the cylindrical body.

The invention also provides for a multipurpose catheter characterized in that the inclination of the conical profile of the end is intended to lie in the continuation of the instruments or mandrins when they have a conical end.

The invention also provides for a multipurpose catheter characterized in that the balloon is fixed on the cylindrical body in immediate proximity to the cone of the end and more particularly at the widest base of the cone, that is to say the one furthest from the end of the catheter.

The invention also provides for a multipurpose catheter intended to permit various interventions, comprising a cylindrical body of small diameter which has, at one of its ends, connection mechanism which communicates with non-coaxial channels formed in the inner part of the cylindrical body in such a way that at least one of the channels supplies, to the end remote from that bearing the connection mechanism, a balloon which is able to deform elastically under the effect of a pressure, characterized in that the connection mechanism includes a head made of rigid plastic material and equipped with three independent inlets which each communicate by way of a sealed mechanism in one of the channels of the cylindrical body, in order to permit introduction either of liquid products or of a range of surgical mandrins and/or other instruments, or both simultaneously at the different operating sites.

The invention also provides for a multipurpose catheter characterized in that the connection mechanism includes a head made of rigid plastic material and equipped with three independent inlets which each open into an internal bore via bores, the bores being provided to receive through a sealed mechanism the external profile of the cylindrical body such that the bores of each independent inlet communicate via holes passing through the cylindrical body and/or the sealed mechanism with the non-coaxial channels so that the channels permit introduction either of liquid products or of a range of surgical mandrins and/or other instruments, or both simultaneously at the different operating sites.

The invention also provides for a multipurpose catheter characterized in that the sealed means consist of a first ring which is arranged around the cylindrical body opposite the inlet in a shoulder of the bore, and a second ring which is placed around the said cylindrical body in the continuation of the first, in such a way as to cooperate with the bores of the head.

The invention also provide for multipurpose catheter characterized in that the sealed mechanism includes a ring which is arranged around the cylindrical body opposite the inlet in a shoulder of the bore, while the external diameter of the body is directly fixed in the bore of the head.

The invention also provides for a multipurpose catheter characterized in that the rings are bonded on the external profile of the cylindrical body and on the internal periphery of the bores in order to make the head integral with the body.

The invention also provides for a multipurpose catheter characterized in that the ring has a length which is defined in order to delimit, in the shoulder of the bore, a chamber which communicates with the bore of the inlet of the head via a space.

The invention also provides for a multipurpose catheter characterized in that the space is provided solely on the inlet side of the head, while the outer wall of the cylindrical body is in tight contact, on the one hand with the internal periphery of the bore and, on the other hand, opposite the space, with the internal periphery of the bore.

The invention also provides for a multipurpose catheter characterized in that the cylindrical body has two non-coaxial channels of different diameters which are offset in relation to each other and laterally in relation to the main axes of the body, in such a way that the first channel communicates with two inlets of the head, while the second channel cooperates with the third inlet for supplying the sealing mechanism.

The invention also provides for a multipurpose catheter characterized in that the cylindrical body has at least three non-coaxial channels of different diameters which are offset in relation to each other and laterally in relation to the main axes of the body, in such a way that the first channel of greater diameter communicates with the first inlet of the head, the second channel with the third inlet of the head for supplying the sealing mechanism, and the third channel with the second inlet for emerging from the body at the same level as the first channel.

The invention also provides for a multipurpose catheter characterized in that the cylindrical body has a hole to permit communication between the channel and the bore of the inlet.

The invention also provides for a multipurpose catheter characterized in that the cylindrical body has a hole permitting communication between the channel and the bore of the inlet.

The invention also provides for a multipurpose catheter characterized in that the cylindrical body has two channels which communicate via holes in the chamber connected to a space in order to open into the bore of the second inlet of the head in order to supply the sealed mechanism.

The invention also provides for a multipurpose catheter characterized in that the range of instruments includes of mandrins cooperating with the channels of the cylindrical body in order to perform various tests or operations.

The invention also provides for a multipurpose catheter characterized in that the surgical mandrins include a head integral with a rod whose free end varies in its geometric shape and its material.

The invention also provides for a multipurpose catheter characterized in that the mandrin has a free end designed with a hemispherical profile.

The invention also provides for a multipurpose catheter characterized in that the mandrin has a rod of curved profile whose free end is designed with a hemispherical profile.

The invention also provides for a multipurpose catheter characterized in that the cylindrical body is rigid.

The invention also provides for a multipurpose catheter characterized in that the cylindrical body is flexible.

The invention also provides for a multipurpose catheter characterized in that the cylindrical body is transparent.

BRIEF DESCRIPTION OF THE DRAWINGS

The invention also provides for a multipurpose catheter comprising a cylindrical body including a first end, a second end, and at least three internal non-coaxial channels, a connection mechanism disposed adjacent the first end for communicating with the at least three non-coaxial channels, the connection mechanism comprising an ergonomic monobloc head which is sealingly attached to the first end of the cylindrical body, the ergonomic monobloc head comprising a bulged wall having at least three independent inlets for communicating with the at least three non-coaxial channels via bores, two walls which continue from the bulged wall, and a concave inwardly curved connecting wall, the connecting wall being disposed adjacent the first end of the cylindrical body and connecting the two walls, wherein the two walls comprise first opposite facing inclined surfaces and second opposite facing inclined surfaces having a different inclination, one of the at least three internal non-coaxial channels being adapted to provide communication between at least one of the at least three independent inlets and an elastically deformable balloon disposed adjacent the second end, and two of the at least three internal non-coaxial channels being adapted to allow the respective introduction of a liquid and a surgical mandrin, wherein the ergonomic monobloc head is adapted to be gripped by a user.

The catheter may be adapted for use in various medical interventions. Each of the at least three independent inlets may communicate with a corresponding internal non-coaxial channel via a corresponding bore. The catheter may be adapted to simultaneously deliver the liquid and the surgical mandrin via separate internal non-coaxial channels while the balloon is expanded via a different internal non-coaxial channel. The ergonomic head may comprise an injection moldable rigid plastic material. The first opposite facing inclined surfaces may comprise a shorter length than the second opposite facing surfaces and each of the first and second opposite facing inclined surfaces may be inclined inwardly and towards one another. The second end of the cylindrical body may comprise a conical profile. One of the at least three internal non-coaxial channels may comprise a large main channel, the large main channel comprising an axis which corresponds to an axis of the conical profile. The large main channel may be eccentrically disposed with respect to an external diameter of the cylindrical body.

Figure 1:
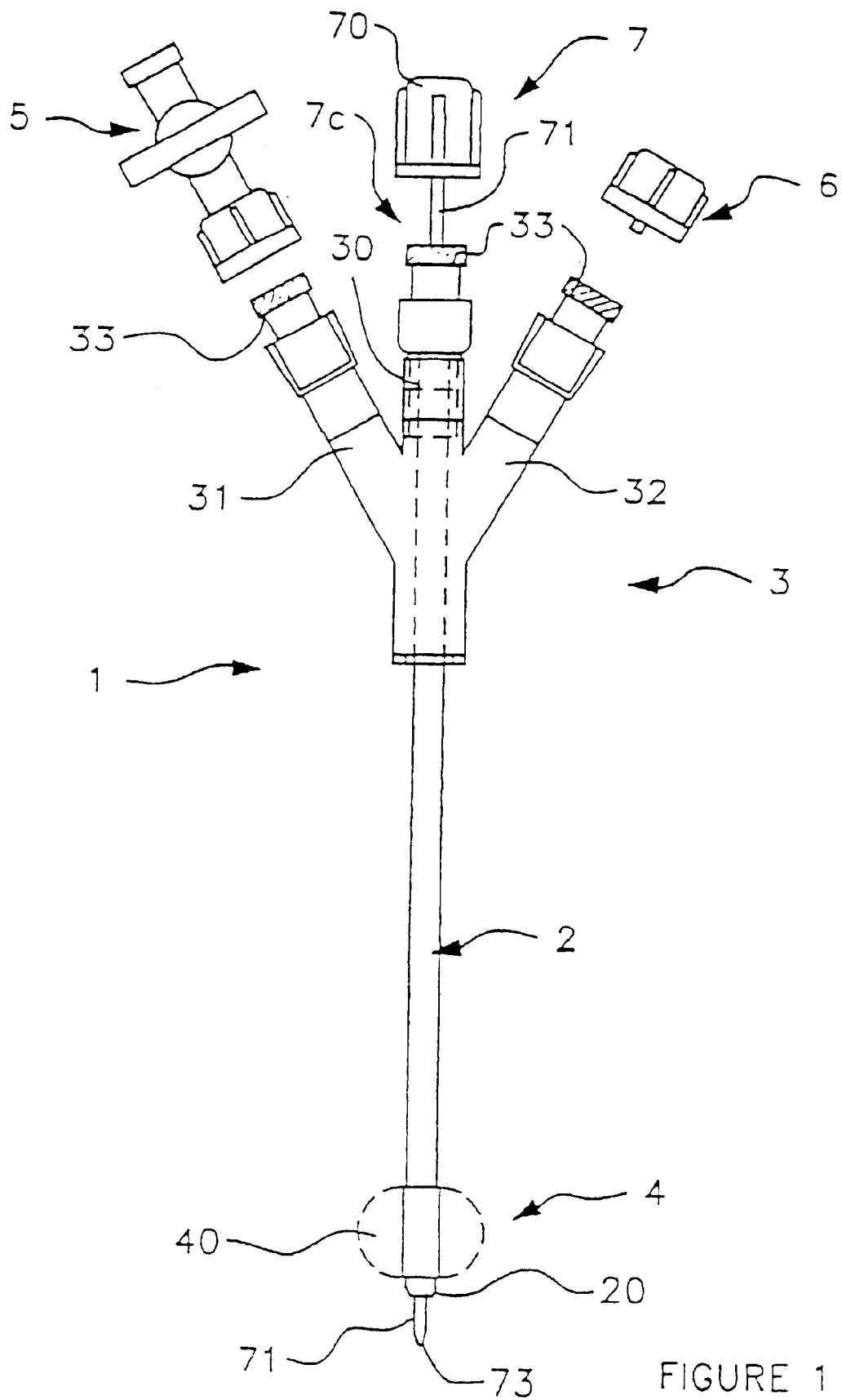

The second end may comprise a cone shaped profile and the balloon may be fixedly disposed in an immediate proximity to the cone shaped profile. The balloon may be disposed in the immediate proximity to a widest diameter portion of the cone shaped profile. The bores of the connection mechanism may comprise separate internal bores, each of the bores providing separate sealed communication between the at least three independent inlets and the at least three internal non-coaxial channels. The first end of the cylindrical body may extend into the connection mechanism. The catheter may be adapted to introduce one of a range of surgical mandrins and a range of surgical instruments into a patient.

The connection mechanism may be connected to the first end of the cylindrical body via a sealing mechanism which comprises a first ring arranged around the cylindrical body. The first ring may be disposed in a bore of the connection mechanism wherein the bore has a shoulder. The connection mechanism may further comprise a second ring arranged around the cylindrical body, the second ring being disposed in another bore of the connection mechanism. The first and second rings may be bonded to each of the cylindrical body and the connection mechanism in order to make the ergonomic monobloc head integral with the cylindrical body. The sealing mechanism may be disposed adjacent the inwardly curved connecting wall. The connection mechanism may comprise a chamber disposed in the area of the first ring and the shoulder of the bore. The connection mechanism may comprise a space which communicates with the chamber and at least one of the at least three independent inlets.

Two of the at least three internal non-coaxial channels may comprise different diameters, and wherein each of the two internal non-coaxial channels are offset in relation to each other. Each of the two internal non-coaxial channels may be laterally offset relative to a main center axis of the cylindrical body and wherein one of the two internal non-coaxial channels communicates with two of the at least three independent inlets and wherein another channel of the two internal non-coaxial channels communicates with another of the at least three independent inlets and the balloon. The at least three internal non-coaxial channels may have different diameters which are offset in relation to each other and offset laterally in relation to a main center axis of the cylindrical body. The at least three internal non-coaxial channels may comprise a first channel, a second channel and a third channel and wherein the at least three independent inlets comprise a first inlet, a second inlet and a third inlet, wherein the first channel communicates with the first inlet, the second channel communicates with the third inlet and the balloon, and the third channel communicates with the second inlet.

The cylindrical body may comprise at least one bore which cooperates with at least one bore in the connection mechanism to permit communication between at least one channel of the at least three internal non-coaxial channels and at least one inlet of the at least three independent inlets. The cylindrical body may comprise a plurality of bores which cooperate with corresponding bores in the connection mechanism to permit communication between the at least three internal non-coaxial channels and the at least three independent inlets. The surgical mandrin may comprise a head which is integral with a rod, the rod having a free end. The free end may comprise a hemispherical profile. The rod may comprise a curved profile. The cylindrical body may comprise a rigid cylindrical body. The cylindrical body may comprise a flexible cylindrical body. The cylindrical body may comprise a transparent material.

The invention also provides for a multipurpose catheter comprising a small diameter cylindrical body including a handle end, a balloon end, and at least a first, a second, and a third internal non-coaxial channel, a connection mechanism disposed adjacent the handle end for communicating with the first, second and third internal non-coaxial channels, the connection mechanism comprising an ergonomic handle head which is sealingly attached to the handle end, the ergonomic handle head comprising a bulged wall having a first, a second and a third independent inlet, each of the first, second and third independent inlets communicating with a corresponding first, second, and third internal non-coaxial channel via first, second, and third bores, two walls which extend from the bulged wall, and a concave inwardly curved connecting wall, the connecting wall being disposed adjacent the handle end of the cylindrical body and connecting the two walls, wherein the two walls comprise first oppositely facing inclined surfaces and second oppositely facing inclined surfaces having a different inclination, the first internal non-coaxial channel communicating with the first independent inlet and an elastically deformable balloon disposed adjacent the balloon end, and the second and third internal non-coaxial channels being adapted to respectively allow introduction of a liquid and a surgical mandrin, wherein the ergonomic handle head comprises an ergonomic shape which is adapted to be gripped by a user.

The description which follows with reference to the attached drawings, given as nonlimiting examples, will permit a better understanding of the invention, of its characteristic features and of the advantages it is likely to afford:

FIG. 1 is a general view representing the multipurpose catheter according to the present invention.

Figure 2:
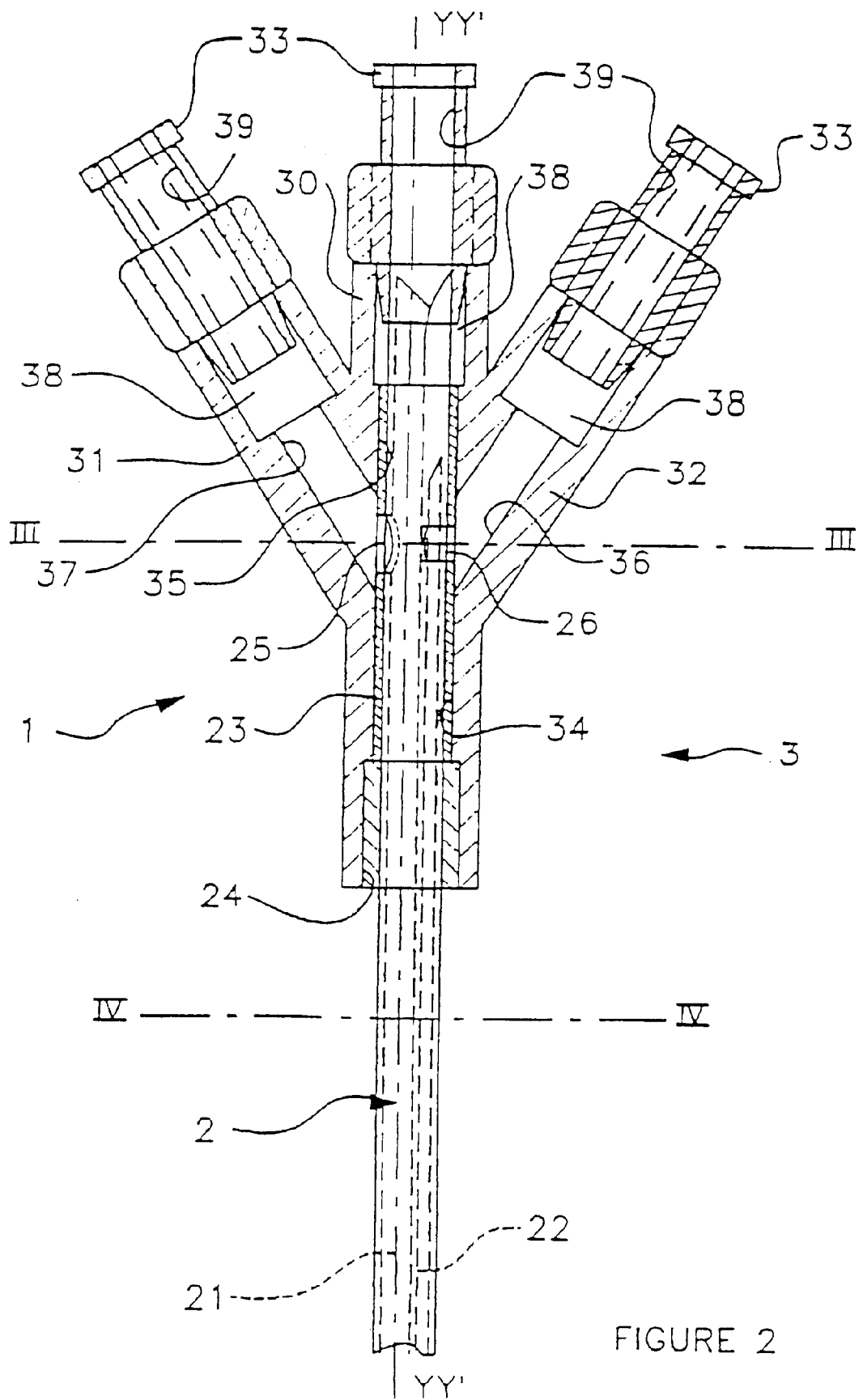

FIG. 2 is a cross section illustrating a first variant of the catheter in which the inlets of the head open into channels of the cylindrical body.

Figure 3:
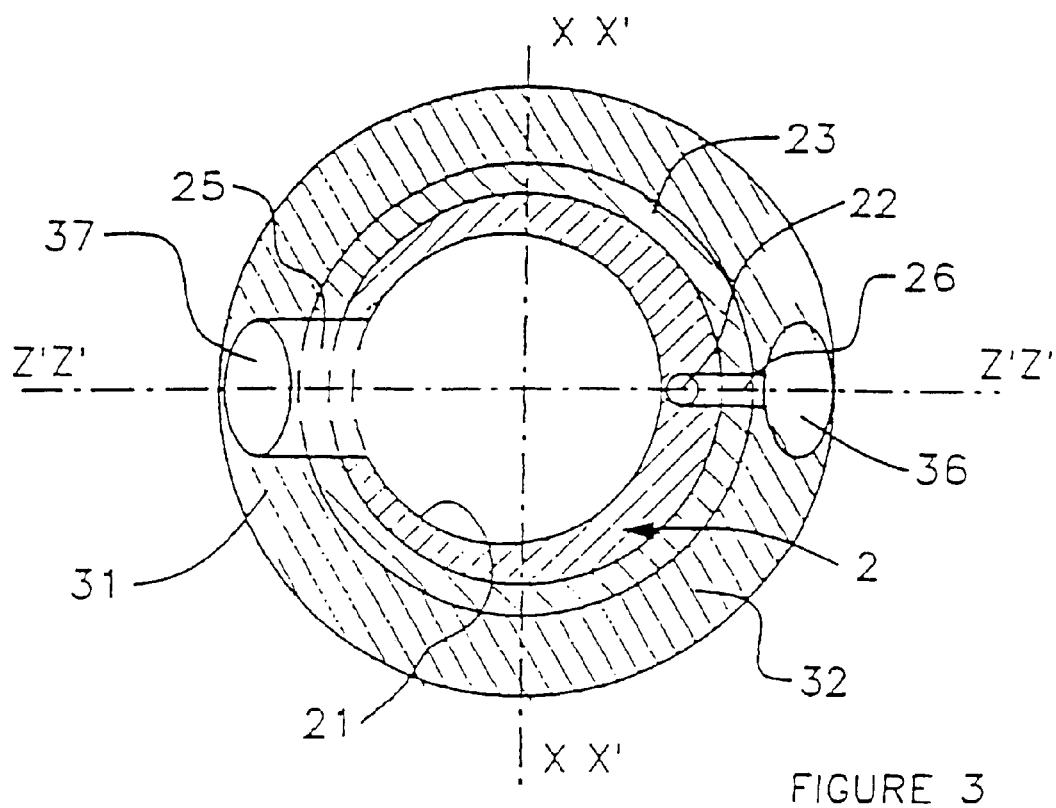
Figure 4:
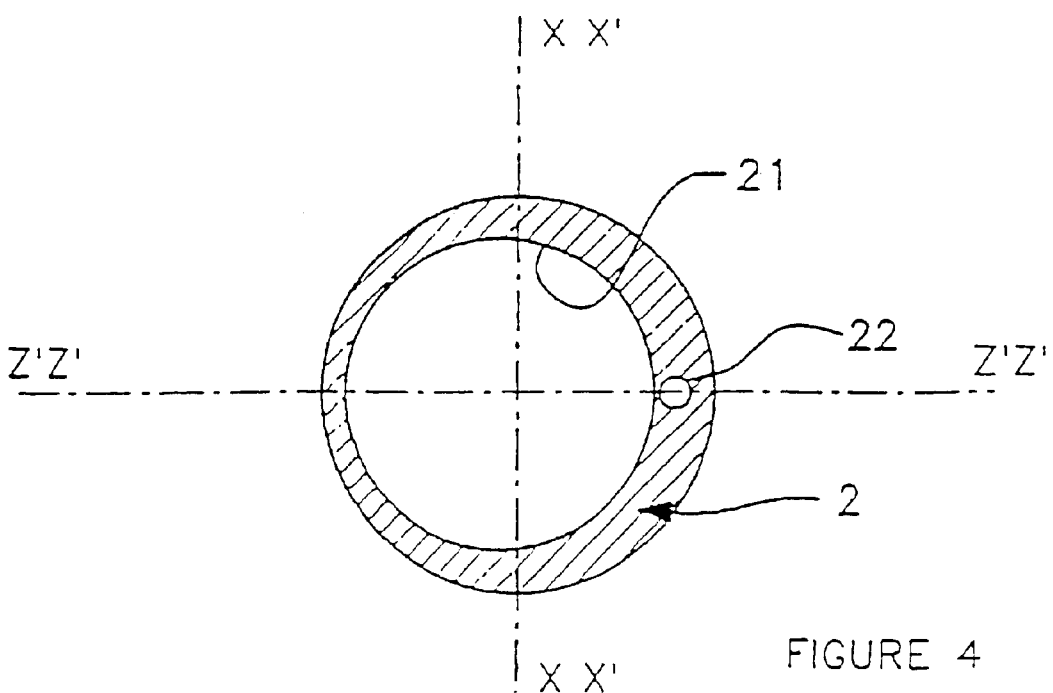

FIGS. 3 and 4 are cross sections along III—III and IV—IV in FIG. 2, showing the position of the channels formed in the cylindrical body of the catheter according to the first variant.

Figure 5:
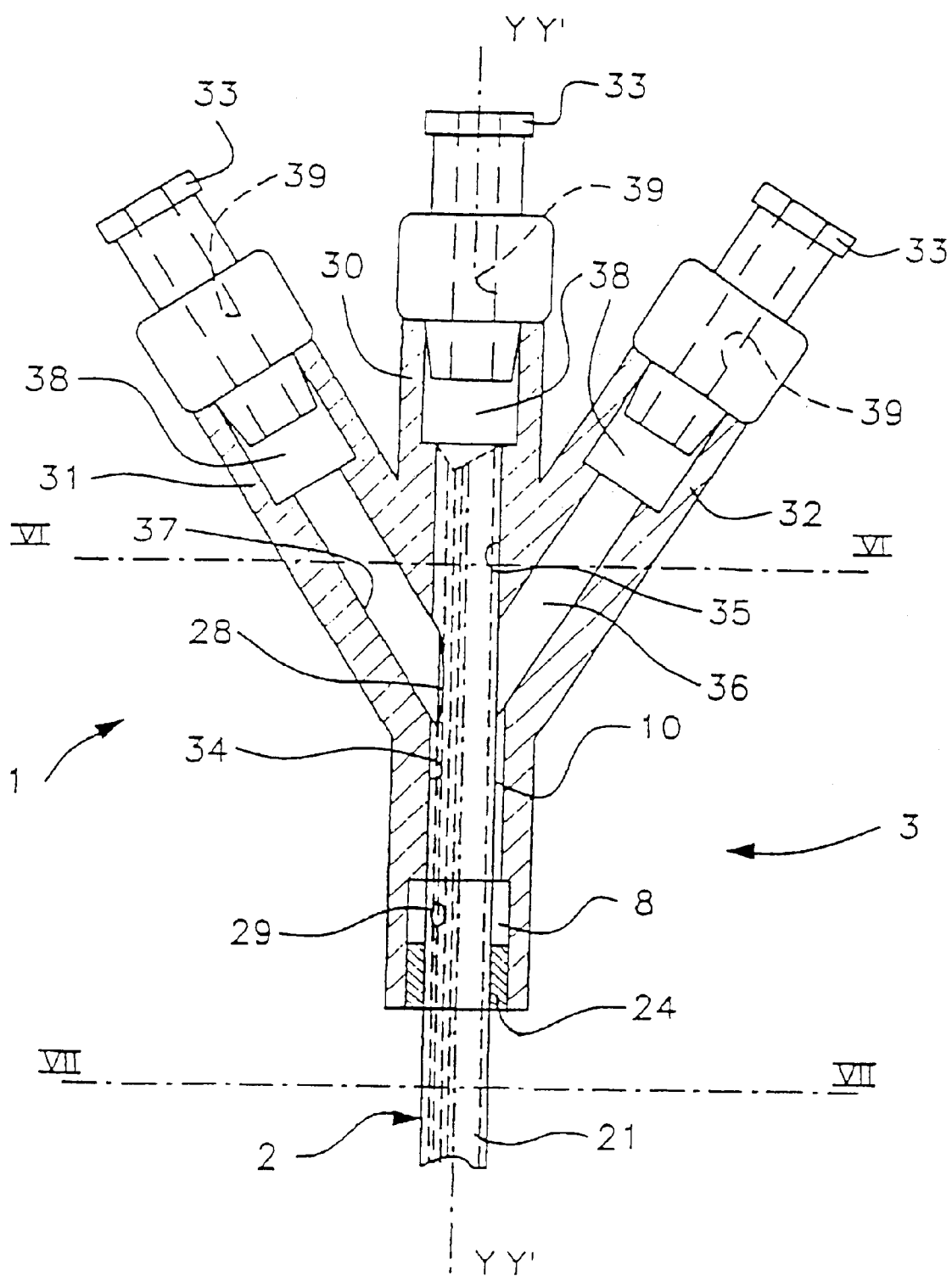

FIG. 5 is a cross section representing a second variant of the multipurpose catheter according to the present invention.

Figure 6:
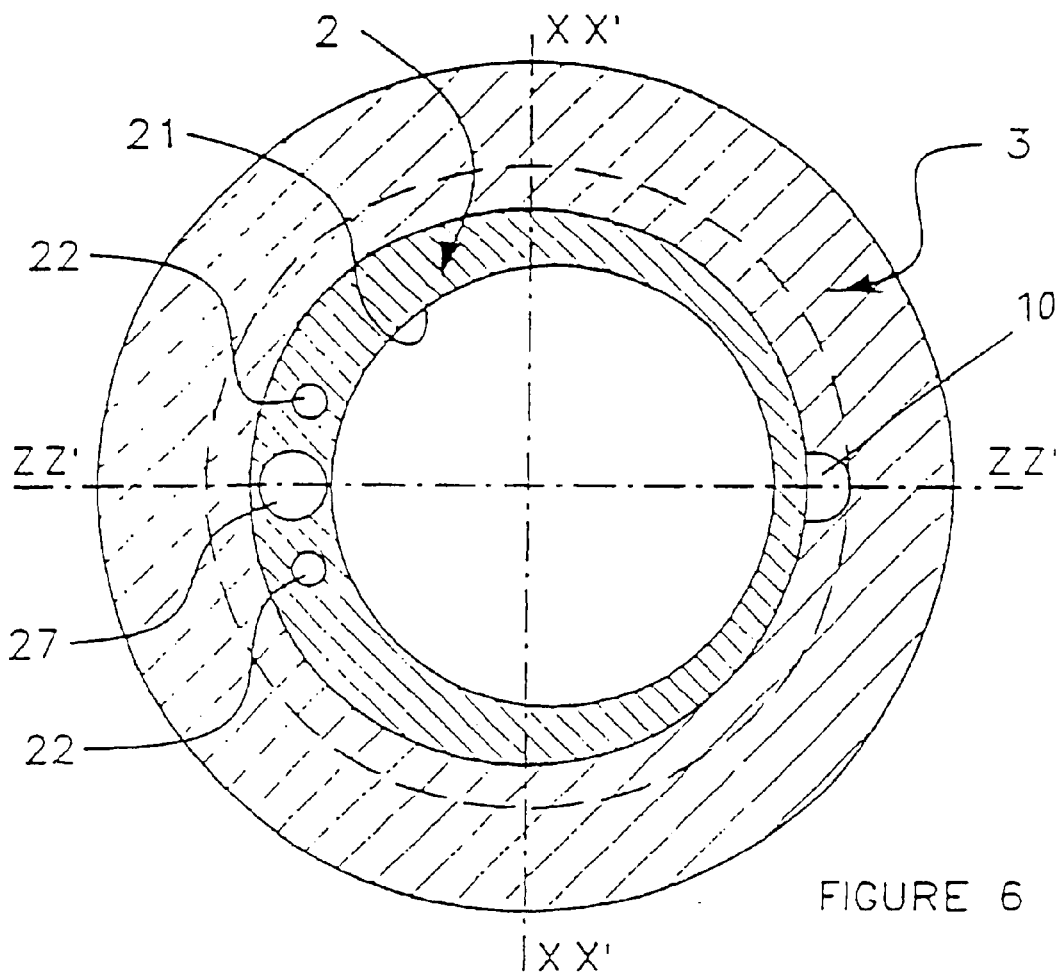
Figure 7:
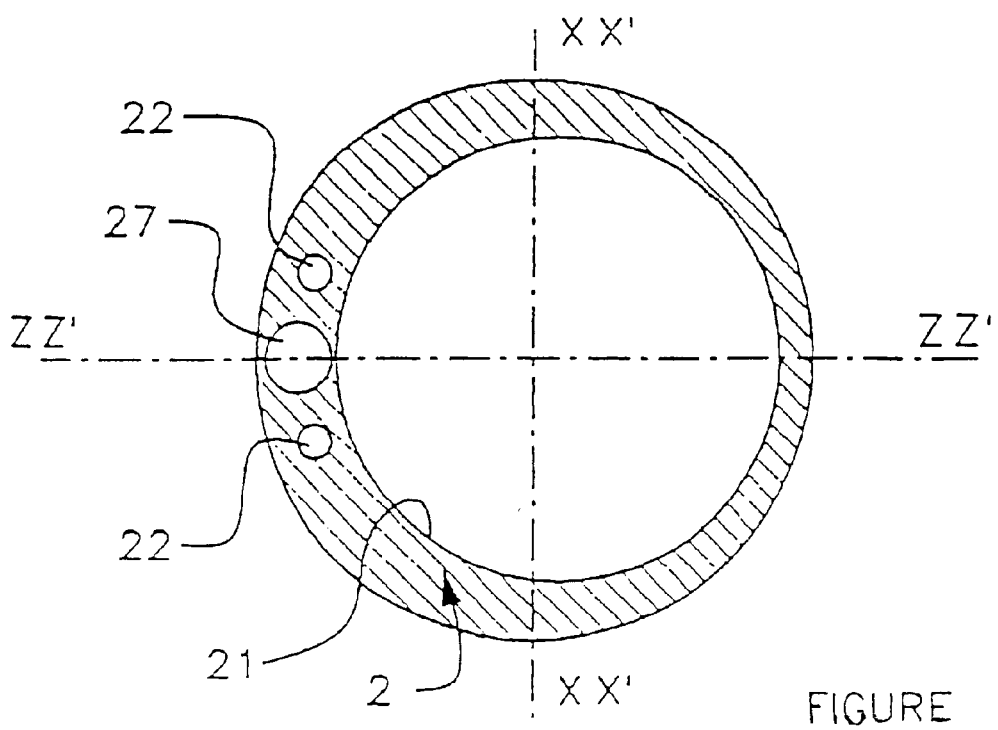

FIGS. 6 and 7 are cross sections along VI—VI and VII—VII in FIG. 5, illustrating another configuration of the channels formed in the cylindrical body of the catheter.

Figure 8:
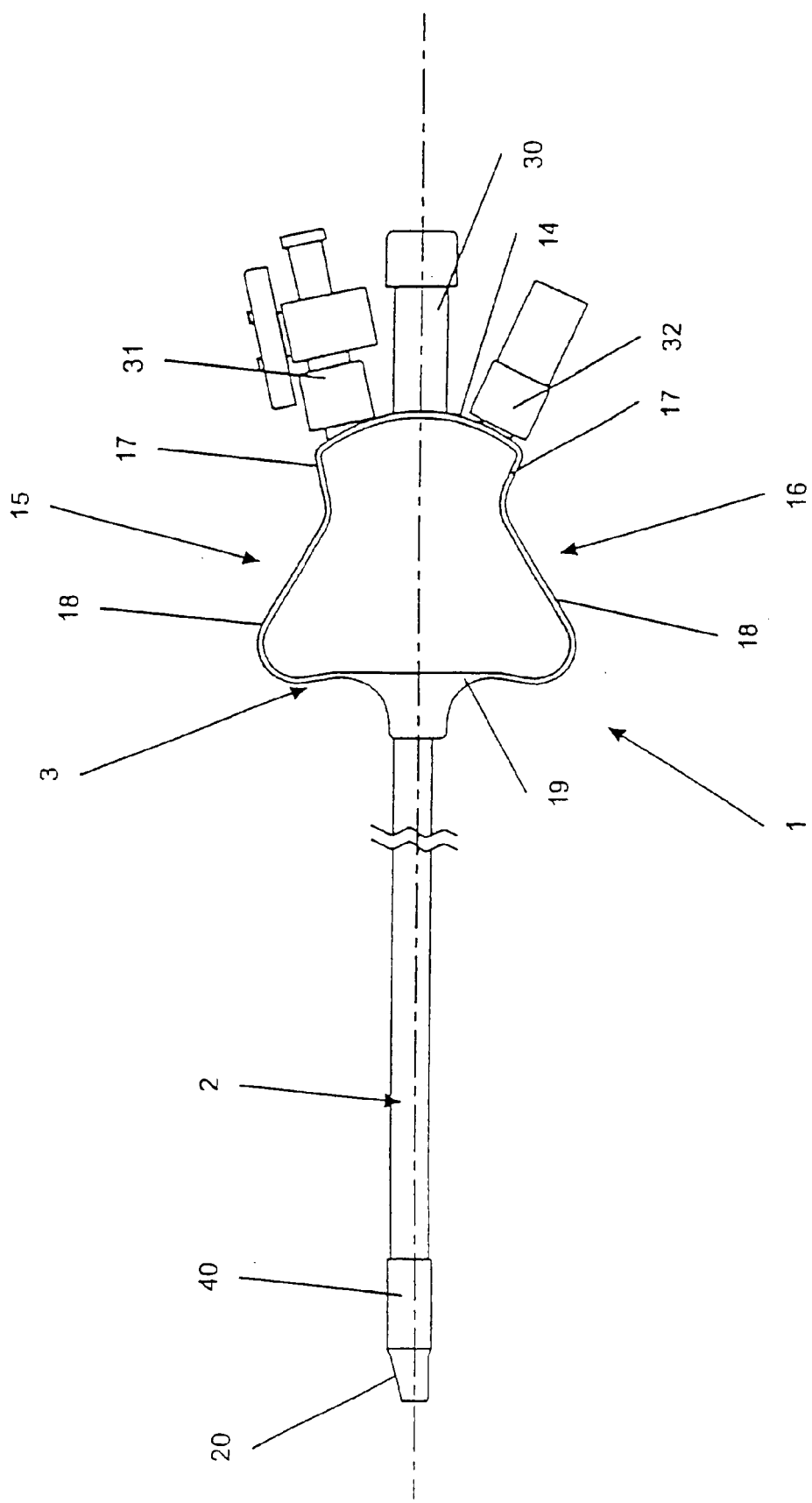

FIG. 8 is a view showing a third variant of the multipurpose catheter, more particularly as regards the profile of the connection head.

Figure 9:
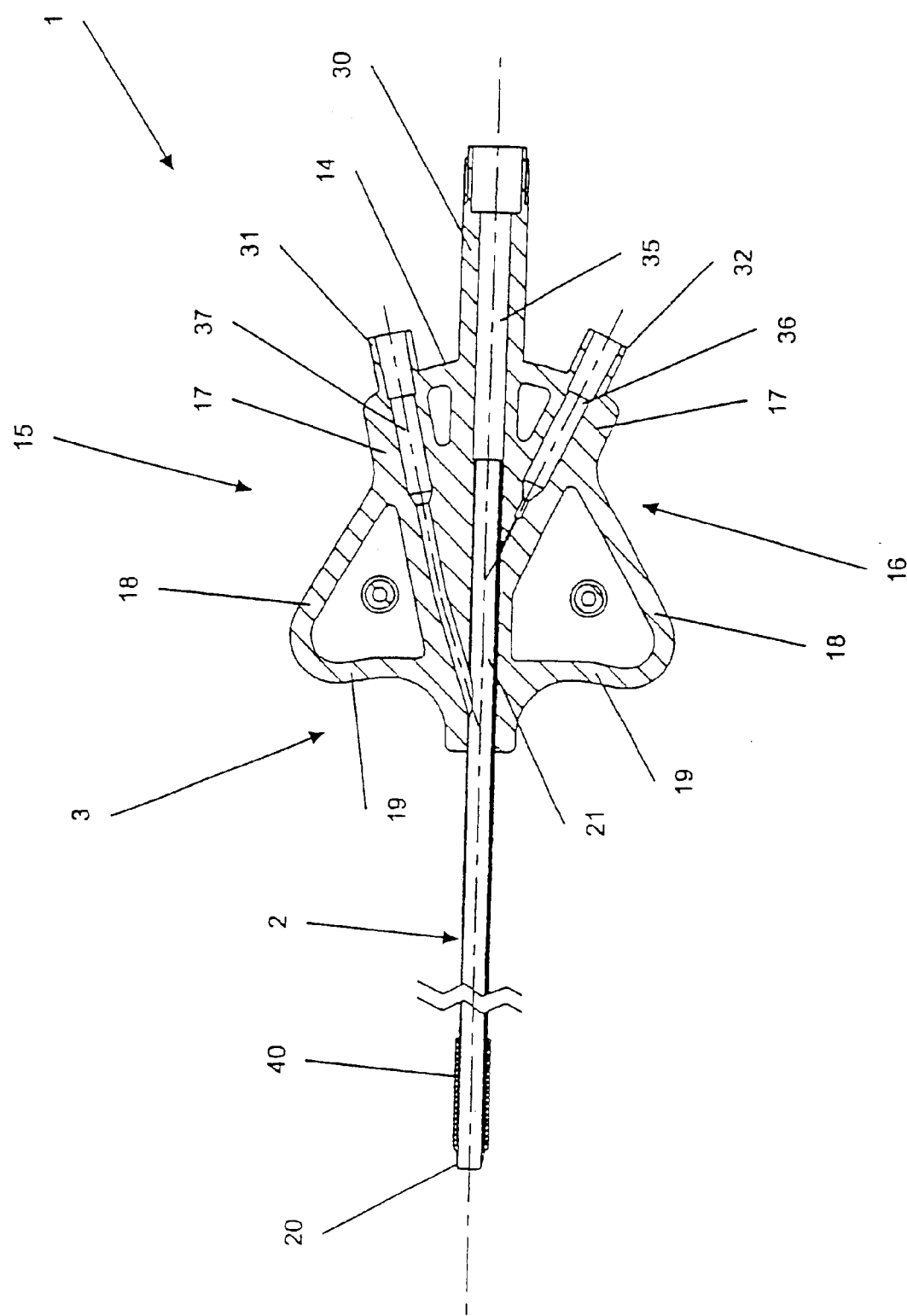
Figure 10:
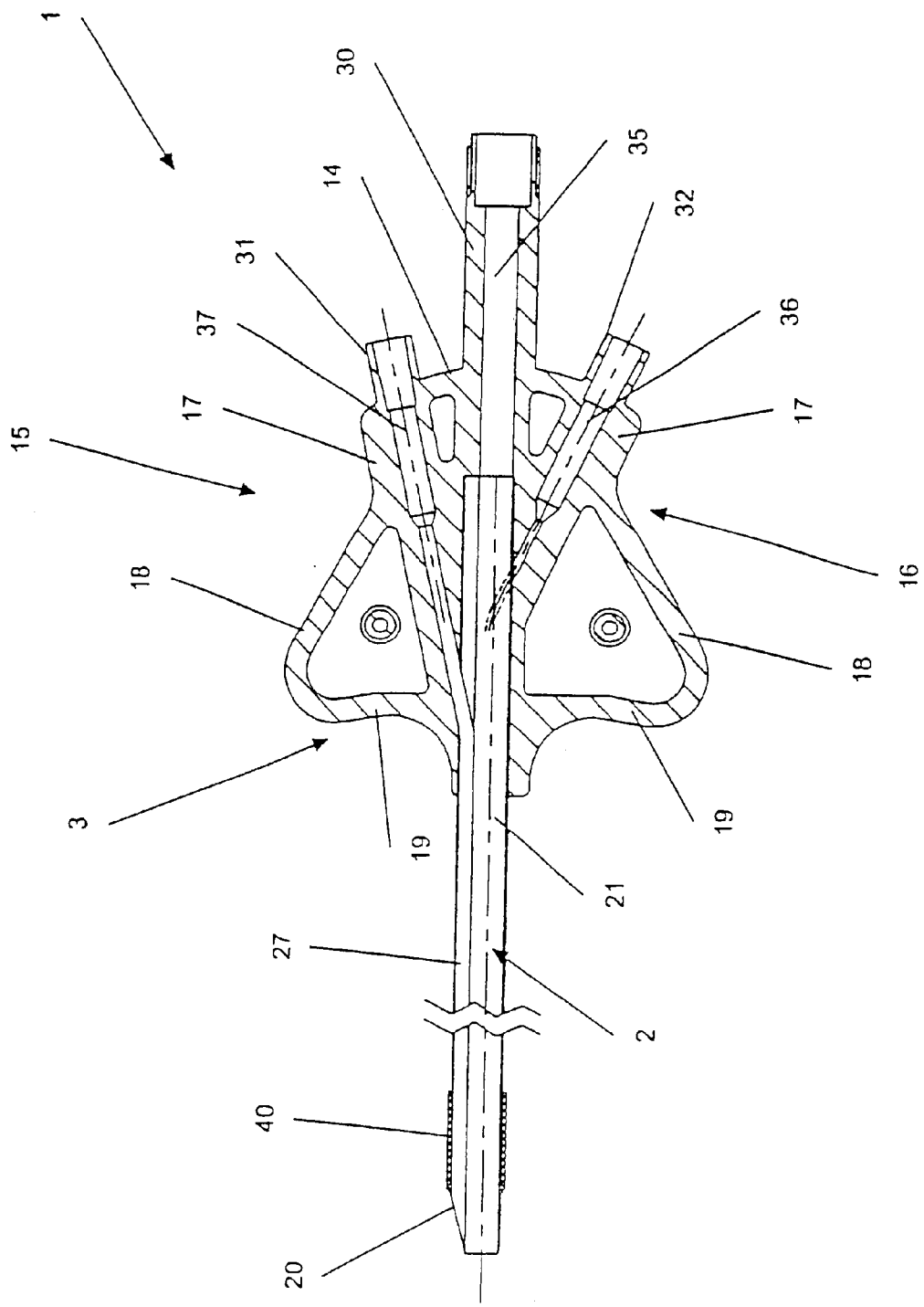

FIGS. 9 and 10 are cross sections representing the connection head according to FIG. 8 and more particularly the position of the independent inlets which cooperate with the non-coaxial channels of the multipurpose catheter.

Figure 11:
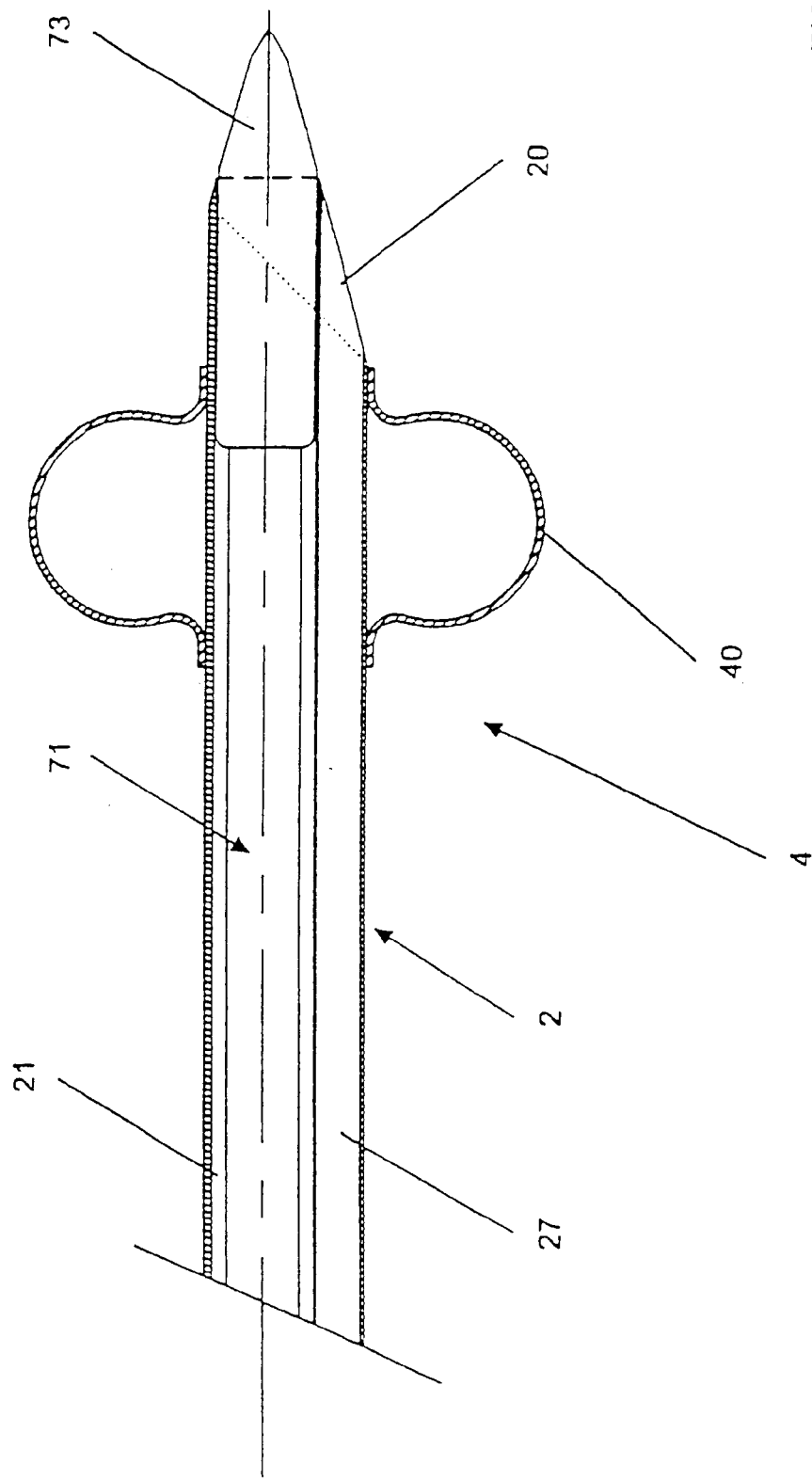

FIG. 11 is a cross section illustrating the profile of that end of the multipurpose catheter remote from the end with the connection head, and the position and the profile of the balloon.

Figure 12:
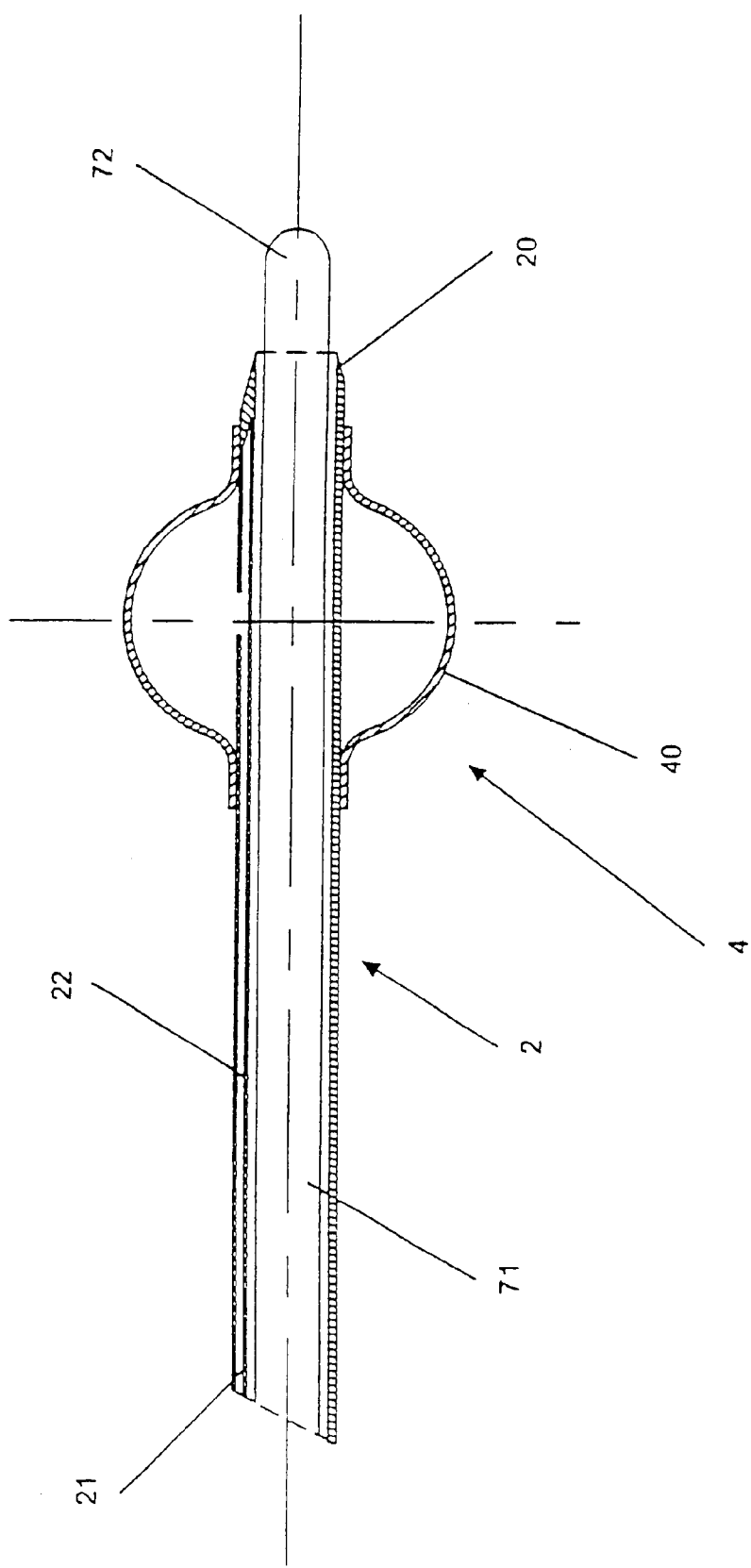

FIG. 12 is a cross section similar to that in FIG. 11 showing another profile of the balloon.

FIGS. 13a, 13b and 14a, 14b are views showing mandrins provided to cooperate with the channels of the catheter in different operations.

Figure 15:
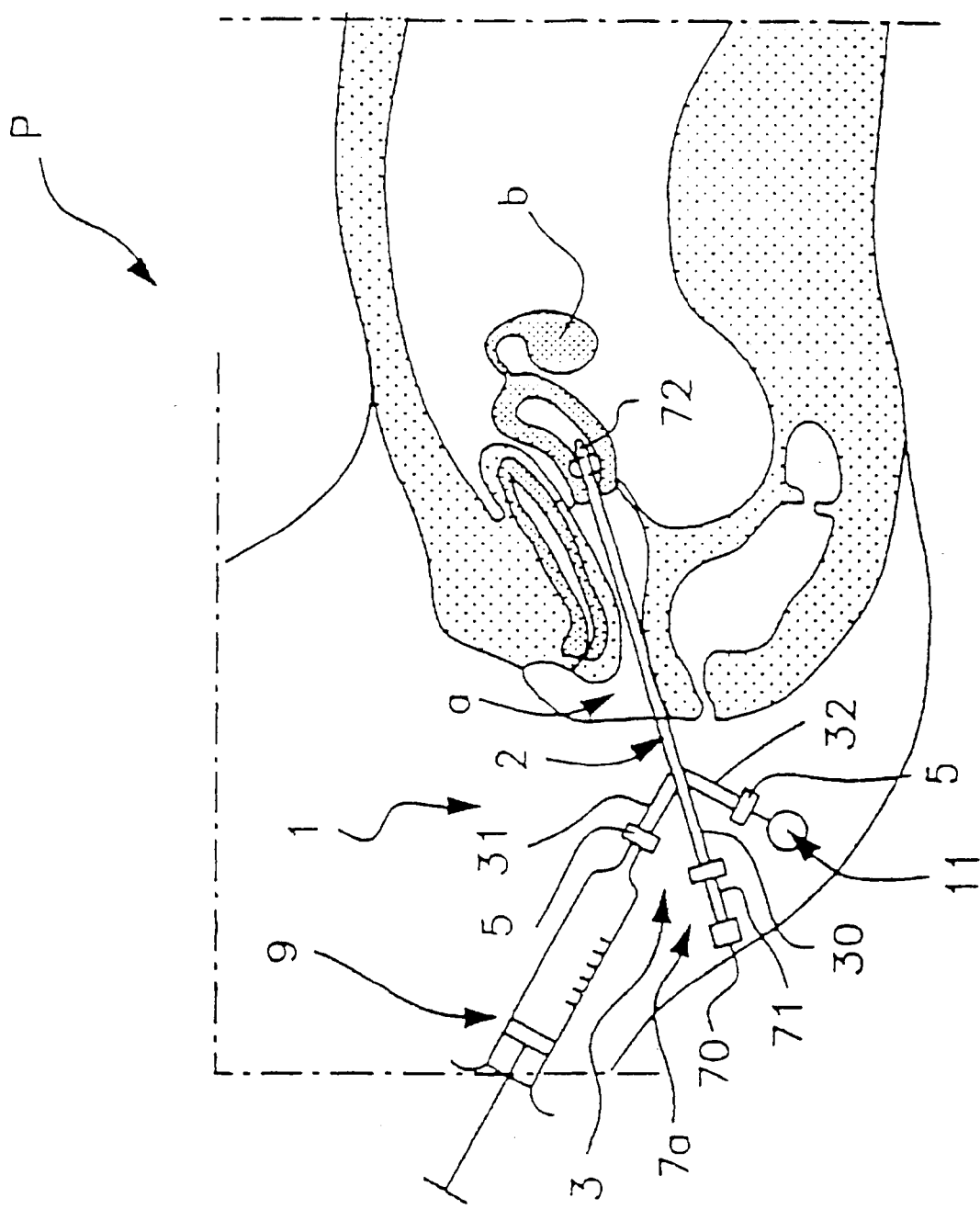

FIG. 15 is a view illustrating an example of use of the multipurpose catheter according to the present invention.

Figure 16:
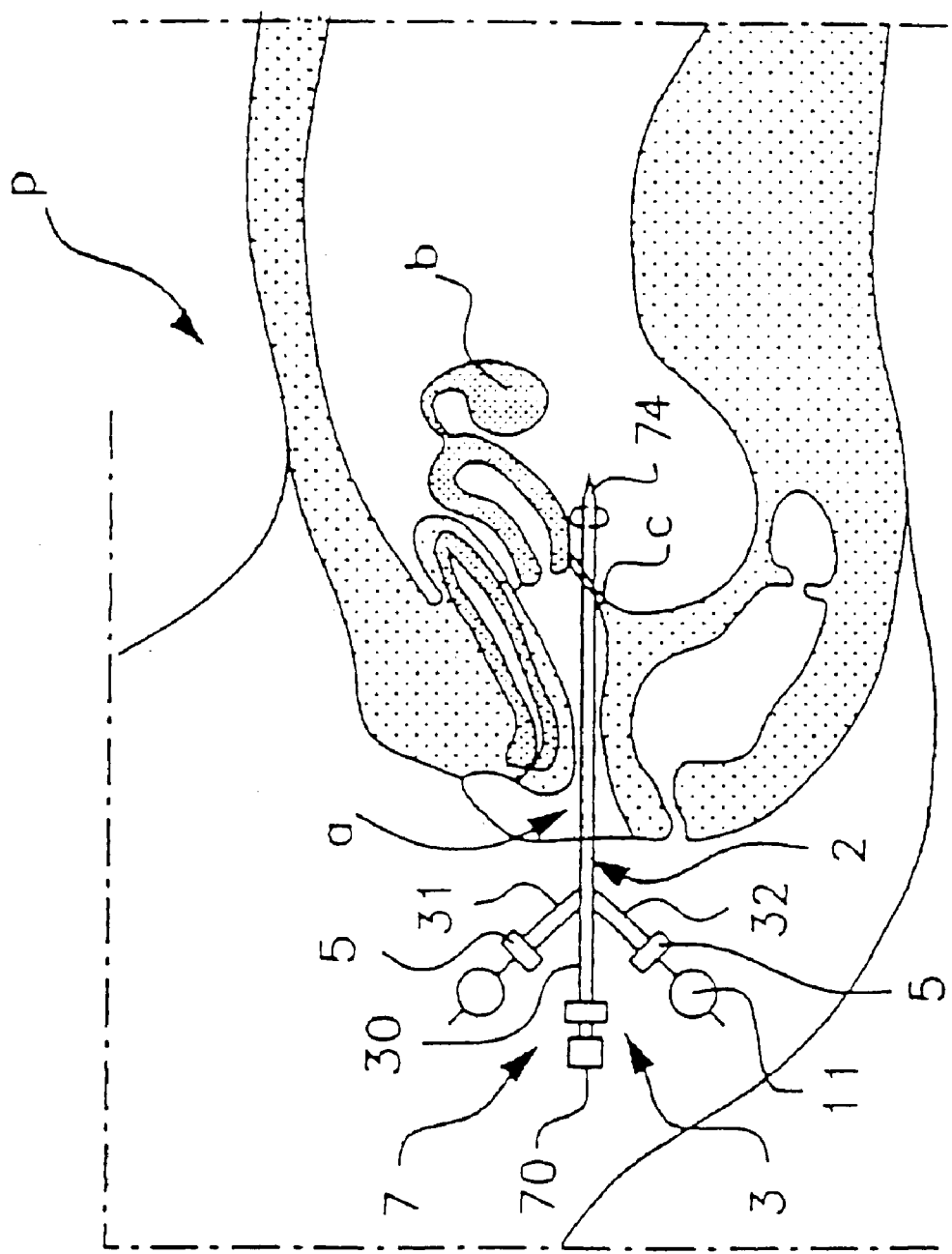

FIG. 16 is a view similar to that of FIG. 15, but representing another example of use of the catheter according to the present invention.

Figure 17:
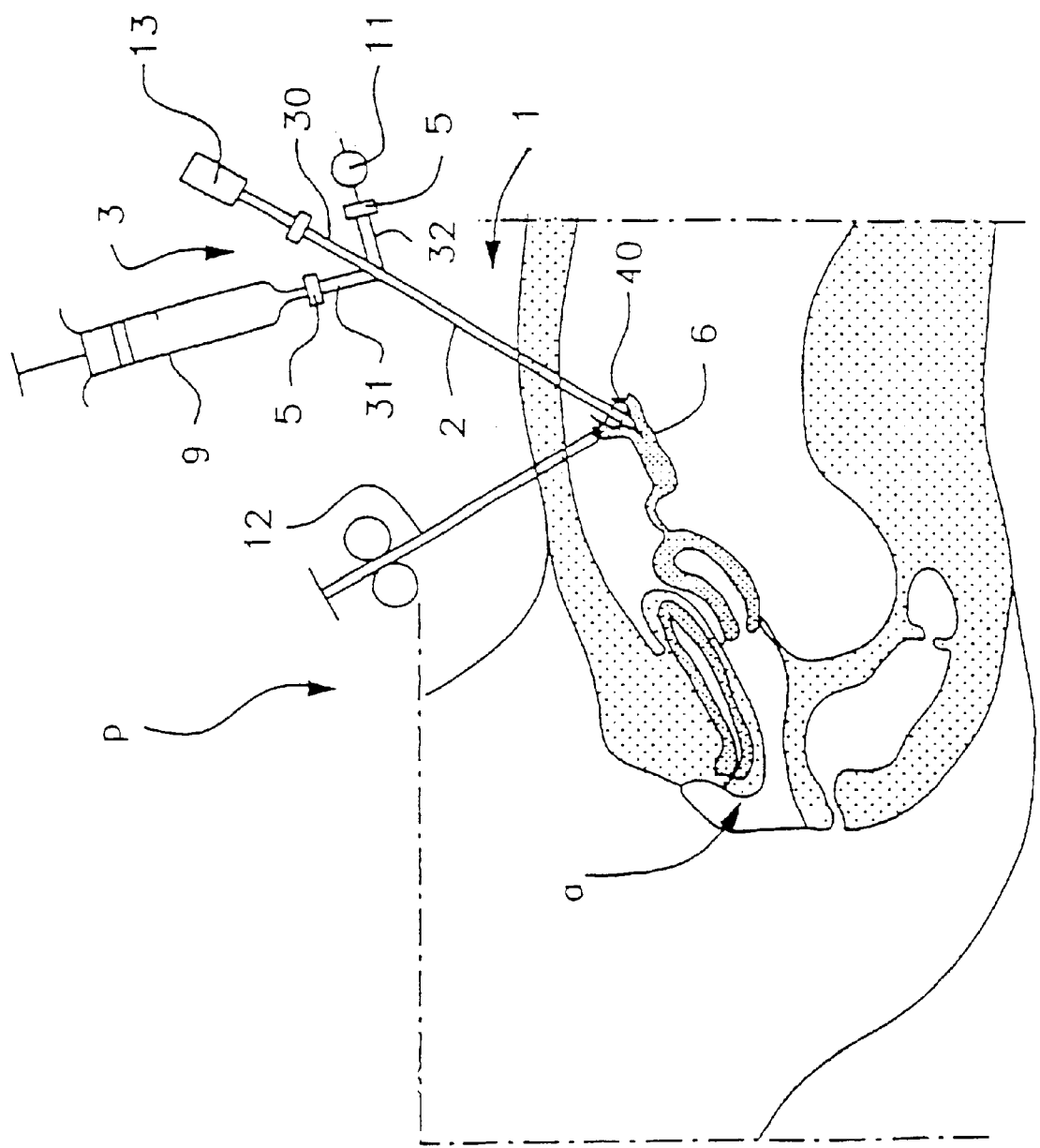

FIG. 17 is a view showing the use of the multipurpose catheter as a trocar during laparoscopy.

Figure 18:
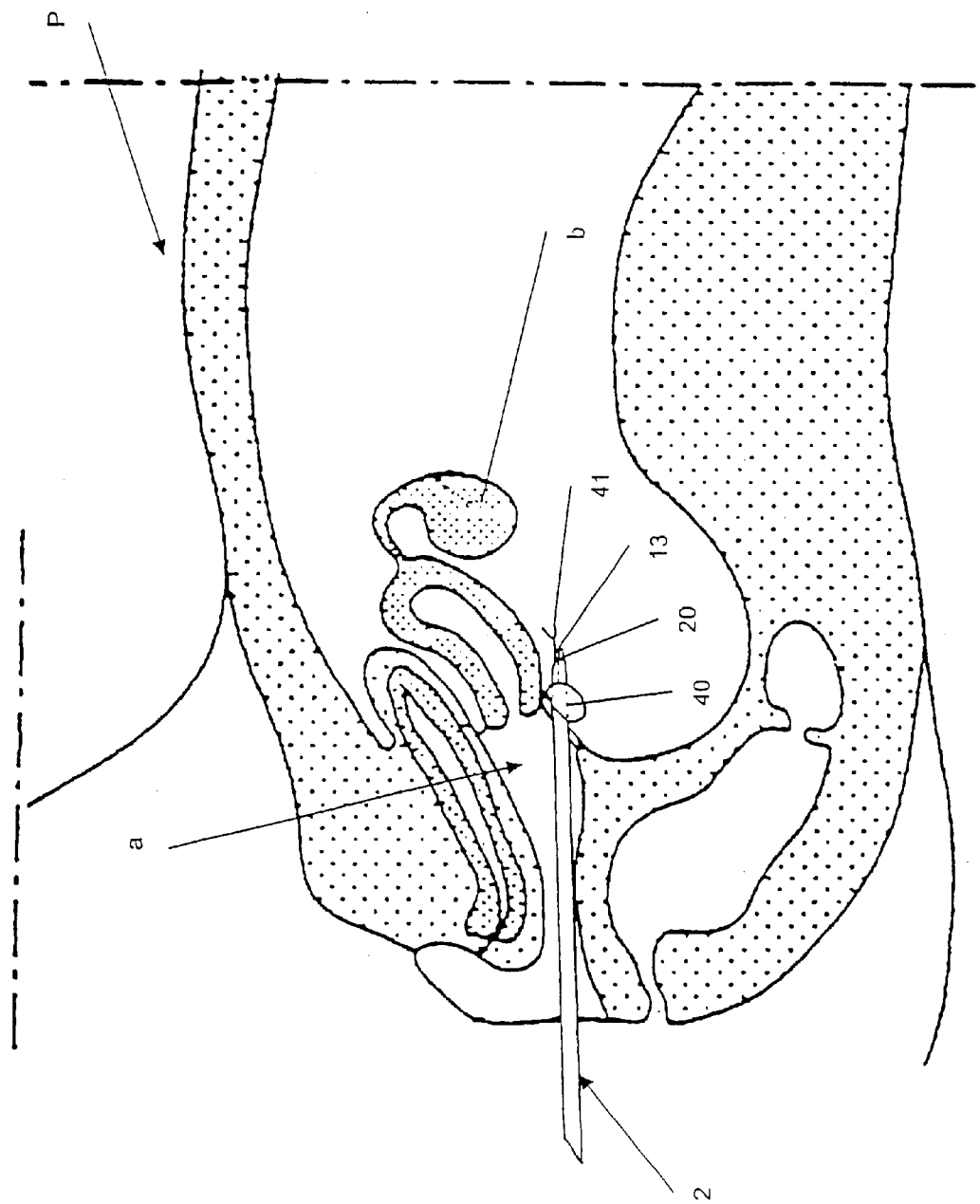

FIG. 18 is a view representing another application concerning the use of the multipurpose catheter according to the invention.

DETAILED DESCRIPTION OF THE INVENTION

In FIG. 1, a catheter 1 is shown which utilizes a cylindrical body 2 of translucent plastic material which is substantially flexible or rigid and integral at one of its ends with a head 3 forming a connection mechanism and including three independent inlets 30, 31 and 32.

At the end remote from the one bearing the head 3, the cylindrical body 2 has sealing mechanism 4 utilizing a balloon 40 which can deform elastically under the effect of a pressure.

Near the balloon 40, the free end of the cylindrical body 2, ends with a tapered profile 20 in a point (FIGS. 11, 12).

The connection head 3 is made of a rigid plastic material which may or may not be transparent and whose inner part is hollow in such a way that each inlet 30, 31 and 32 opens into channels formed in the cylindrical body 2.

The connection head 3 is monobloc and has a double Y-shape forked profile, that is to say the inlet 30 is on the same longitudinal axis as that of the cylindrical body 2, while the other two inlets 31 and 32 are offset laterally so as to be arranged to each respective side of the inlet 30.

The inlets 30, 31 and 32 are each integral with a joining element 33 which permits sealed attachment, for example, of a valve 5 for introduction of liquids, a stopper 6 obstructing an inlet, and the positioning of a series of surgical mandrins 7 whose profiles vary depending on the intervention.

In FIGS. 2 to 4, a first variant of the multipurpose catheter 1 is shown whose cylindrical body 2 has two channels 21 and 22 running along its length, and along longitudinal axes offset in relation to the main axes XX' and YY'.

It will be noted that the diameter of the main channel 21 is greater than that provided for the channel 22 and that these channels are arranged on at least one main axis ZZ' of the cylindrical body 2 (FIG. 4). The channels 21 and 22 are also offset in relation to one another. Furthermore, the channel 21 is eccentric in relation to the external diameter of the cylindrical body 2.

The head 3 has an internal bore 34 which opens out into each inlet 30, 31 and 32 via a bore 35, 36 and 37. The inlets 30, 31 and 32 each comprise a chamber 38 into which opens, on the one hand, each bore 35, 36 and 37, and on the other hand, the joining elements 33.

The joining elements 33 have an internal bore 39 which communicates with the chamber 38 of each inlet 30, 31 and 32 of the head 3.

The head 3 is attached to the cylindrical body 2 in a sealed manner by way of a first ring 24 which is arranged around the body and opposite the inlet 30 in a shoulder of the bore 34 which is provided with a diameter greater than this bore.

A second ring 23 is placed around the cylindrical body 2 in the continuation of the first one, in such a way as to cooperate with the bores 34 and 35 of the head 3. The rings 23 and 24 are bonded on the external profile of the cylindrical body 2 and on the internal periphery of the bores 34 and 35 in order to Lake the connection head 3 integral with the body.

The two rings 23 and 24 are provided with different external diameters, while their internal diameter is identical in order to cooperate coaxially around the cylindrical body 2.

The cylindrical body 2 passes through the chamber 38 of the inlet 30 to allow the channel of large diameter 21 to open into the bore 39 of the corresponding joining element 33.

At the opposite end, the main channel 21 emerges from the cylindrical body 2 along the tapered profile 20 of pointed or conical shape.

It will be noted that the end 20 of the cylindrical body 2 has a conical profile which is arranged on the axis of the main channel 21. The latter is eccentric in relation to the external diameter of the cylindrical body 2, which gives this particular profile to the end 20 (FIGS. 11, 12).

Thus, the end 20 has a conical profile which has an inclination of about 30° [sic] degrees.

The conical profile of the end 20 is intended to be disposed in the continuation of the instruments or mandrins 7 whose end is also conical.

It will be noted that the balloon 40 is fixed on the cylindrical body 2 of the catheter in immediate proximity to the cone of the end 20, and more particularly at the widest base of the cone, that is to say the one furthest from the end of the catheter (FIGS. 11, 12).

The ring 23 and the cylindrical body 2 have a first through-hole 25 allowing the bore 37 of the inlet 31 to communicate with the channel of large diameter 21.

The inlet 31 cooperates with a leaktight stopper (not shown) which, by being clamped onto the threaded part of the inlet 31, forms a leaktight seal with the mandrin or the instrument introduced into the channel 21.

Thus, it will be noted that two inlets 30 and 31 open into the same channel 21 formed in the inner part of the cylindrical body 2.

Likewise, the ring 23 and the cylindrical body 2 have another through-hole 26 situated opposite the first one 25 for allowing the bore 36 of the inlet 32 to communicate with the channel of smaller diameter 22. The latter, arranged parallel to the channel 21, is intended to open out in the area of the sealing mechanism 4 in order to inflate the balloon 40.

It will be noted that the multipurpose catheter 1 described above is of the type with three inlets and two routes, that is to say two inlets open into the same channel.

In FIGS. 5 to 7, a second variant of the multipurpose catheter 1 is shown whose cylindrical body 2 has, in addition to the channels 21 and 22, another channel 27 arranged on axes which are offset laterally in relation to the main axes XX' and YY' of the cylindrical body 2, and offset in relation to those of the channels 21 and 22.

In this variant there are two channels 22 which run, on either side of the channel 27, between the latter and the channel 21. It will be noted that the channels 22 are on one and the same axis which is parallel to the axis XX' of the cylindrical body 2, but arranged in a different vertical plane, as is shown in FIG. 7.

It will be noted that the channels 21 and 27 are arranged on the same axis ZZ' of the cylindrical body 2 (FIG. 7).

The cylindrical body 2 is integral with the head 3 described above and equipped with its three independent inlets 30, 31 and 32.

It will be noted that the inlets 30, 31, 32 are integral with the joining element 33, in order to delimit the chamber 38.

The cylindrical body 2 is integral with the head 3 by way of the ring 24, as has been described above, while in this variant the external diameter of the body 2 is bonded directly into the bore 35.

It will be noted that the ring 24 is shorter in length than that described above in order to delimit, in the shoulder of the bore 34, a chamber 8 which the cylindrical body 2 passes through.

Removal of the ring 23 makes it possible to form a longitudinal channel 10 (FIGS. 5 and 6) in the bore 34 in such a way as to bring the chamber 8 into communication in order to supply the channels 22 for inflating the balloon 40.

The longitudinal channel 10 is provided solely on the inlet side 32, so that the outer wall of the cylindrical body 2 is in tight contact on the one hand on the internal periphery of the bore 35 and, on the other hand, opposite the longitudinal channel 10, on the internal periphery of the bore 34 so that the bore 37 of the inlet 31 cannot communicate with the chamber 8.

At the bore 37 of the inlet 31, the cylindrical body 2 has a first through-hole 28 which permits communication between the bore 37 and the channel 27.

In this variant, the channels 21 and 27 emerge at the side remote from the head 3 and more particularly at the tapered pointed end 20.

It will be noted that the cylindrical body 2 has, in the area of the chamber, through-holes 29 which communicate with the channels 22. Thus, the inlet 32 is connected via its bore 36, the longitudinal channel 10, the chamber 8, holes 29 and channels 22, with the balloon 40 which is arranged on the cylindrical body 2 at the opposite end from the head 3, in order to deform it elastically under a pressure.

The catheter 1 described above and shown in FIGS. 5 to 7 has three inlets and three routes or channels compared to the preceding one which had only two routes or channels.

FIGS. 8 to 10 show a third variant of the multipurpose catheter 1 concerning the profile of the connection head 3 on the cylindrical body 2.

The connection head 3 has a highly ergonomic profile allowing the surgeon to easily hold the catheter 1 between the fingers of one hand during various interventions.

The head 3 includes a slightly bulged wall 14 receiving the three independent inlets 30, 31, 32. The wall 14, is arranged perpendicular to the cylindrical body 2 and is continued on each of the said body by a wall 15, 16 with inclined surfaces. Each wall 15, 16 has, in proximity to the inlets 31, 32, an inclined surface 17 of short length which is oriented in the direction of the cylindrical body 2. Each inclined surface 17 is continued by another inclined surface 18 of different inclination and oriented away from the cylindrical body 2. Each inclined wall 18 of the walls 15, 16 meets, at the area of the cylindrical body 2 and opposite the wall 14, via a wall 19 curved inwards in the direction of the body.

Thus, the profile of the connection head 3 permits a better grip by the surgeon in order to precisely introduce the cylindrical body 2 into the different operating sites.

FIG. 9 shows the inner part of the connection head 3 whose inlets 30, 31, 32 cooperate with the non-coaxial channels 21, 22 of the cylindrical body 2, as has been described in FIGS. 2 to 4.

Thus, the connection head 3 allows the inlet 30 to communicate with the channel 21, called the main channel, while the inlet 32 cooperates with the channel 22 to supply the balloon 40.

It will be noted that the inlet 31 also cooperates with the channel 21 of the cylindrical body 2. It will be noted that the inlet 30 comprises an internal bore 35 which is axially offset in order to cooperate with the channel 21, given that the latter is eccentric in relation to the external diameter of the cylindrical body 2 (FIG. 4).

In this embodiment of the connection head 3, it will be noted that the chambers 38 have been omitted, so that each bore 35, 36, 37 of the inlets 30, 31, 32 opens directly into the non-coaxial channels of the body 2 and at the end of the head 3.

In FIG. 10, the inner part of the connection head 3 has been illustrated, where the inlets 30, 31, 32 cooperate with the non-coaxial channels 21, 22, 27 of the cylindrical body 2, as has been described for FIGS. 5 to 7.

Thus, the connection head 3 allows the inlet 30 to communicate with the channel 21, while the inlets 31 and 32 cooperate, respectively, with the channel 27, called the operator channel, for the passage of instruments, and the channels 22 for supplying the balloon 40.

It will be noted that the inlet 31 has an internal bore 37 whose inclination permits communication with the channel 27 via a hole made through the cylindrical body 2.

By contrast, the inlet 32 has an internal bore 36 which is also inclined and turned a quarter of a turn about the axis of the cylindrical body 2 so as to come into communication via holes in the channels 22. This position makes it possible to omit the chamber 8 and the longitudinal channel 10, shown in FIG. 5.

In the solutions described above and shown in Figures [sic] 9 and 10, the connection head 3 is made of injection-molded plastic which attaches directly at the moment of molding around the cylindrical body 2, thereby guaranteeing perfect sealing of the head 3 on the body 2.

In FIG. 11, the end of the cylindrical body 2 is integral with a balloon 40 whose external profile depends on the distance between the points of attachment of the said balloon on the body 2.

Thus, it will be noted that the zones of attachment of the balloon 40 are close together allowing the balloon, when inflated, to present a very rounded profile like a tire, around the cylindrical body 2.

In FIG. 12, the zones of attachment of the balloon 40 are further apart than those shown previously, making it possible to define a volume of the balloon which is different when it is inflated.

The balloon 40 provided at the end of the cylindrical body 2 of the catheter 1 permits sealing by bearing against the wall of the operating site, as will be better seen below. Also, the balloon 40 provides a bearing and a sort of pivoting mechanism which facilitates the movements of the catheter 1 in the space of the operating site and prevents expulsion from the site.

FIGS. 13a, 13b and 14a, 14b show a series 7a, 7b, 7c, 7d of surgical instruments, or mandrins 7, making it possible to carry out the examinations illustrated in FIGS. 15 and 11.

The mandrins 7 in each representation have a head 70 of plastic integral with a metal rod 71 of small diameter.

It will be noted that only the free end opposite the head 70 varies in its geometric shape and its material in order to permit different types [sic] of examination.

Figure 13:
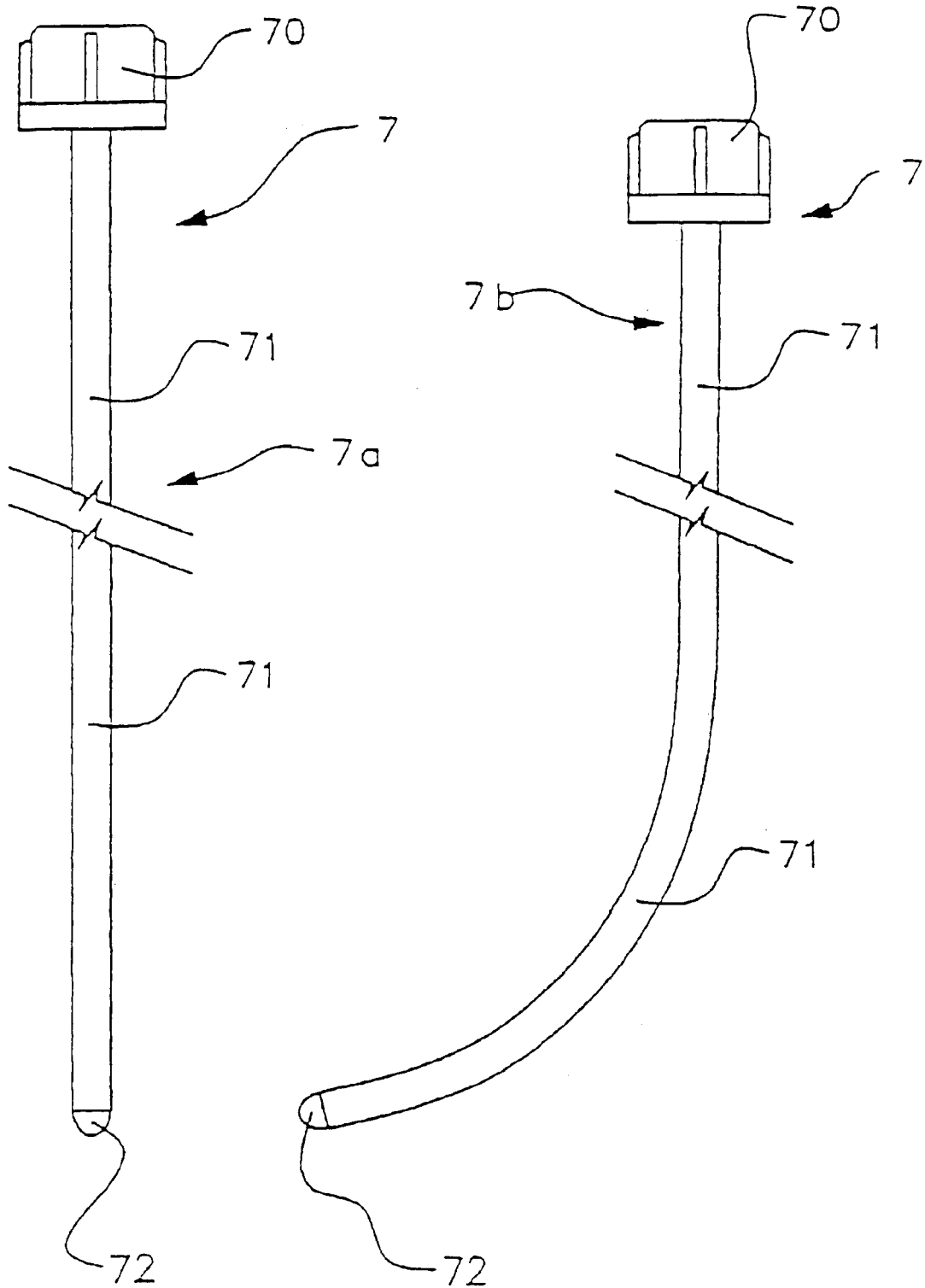

In FIG. 13a, the mandrin 7a has at the end of its rod 71 a free end 72 designed with a hemispherical profile.

In FIG. 13b, the mandrin 7b has a rod 70 presenting a curved profile, but whose free end 72 is designed with a hemispherical profile.

Figure 14:
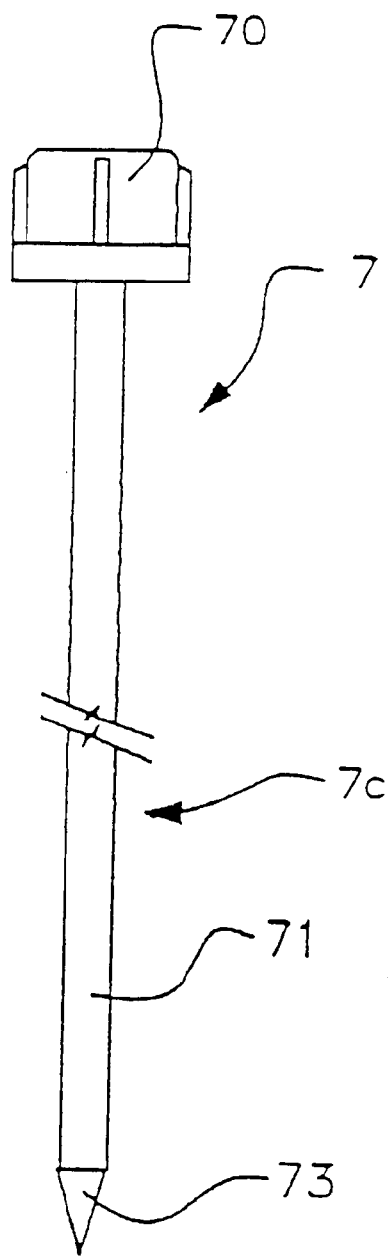
Figure 14:
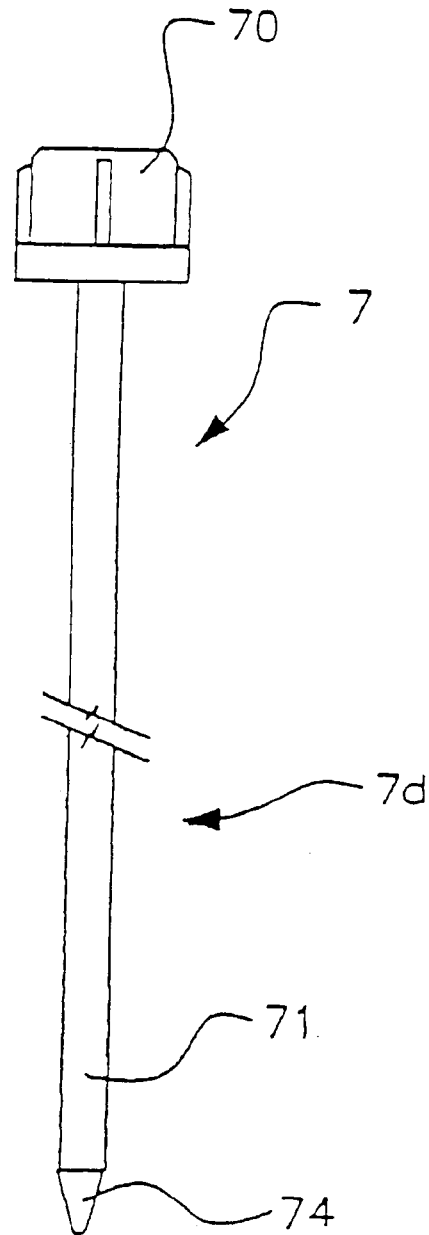

In FIG. 14a, the mandrin 7c has at the end of its rod 71 a free end 73 with a very tapered point or conical shape whose inclination is similar to that of the end 20 of the cylindrical body 2 so as to lie in its continuation (FIG. 11).

Finally, in FIG. 14b, the last mandrin 7d of the series has a free end 74 of conical profile, but the end is slightly rounded. In the same way as before, the conical profile of the end 74 lies in the continuation of the conical end 20 of the body 2.

The multipurpose catheter 1 described above and its mandrins 7a, 7b, 7c, 7d are designed to perform a number of procedures coming under the term FERTILOSCOPY and having of several stages permitting:

evaluation of the state of the uterus,
evaluation of the permeability of the tubes,
evaluation of the ovarian and tube environment,
unparalleled visualization of the distal part of the fallopian tubes and the ovaries,
evaluation of the quality of the fallopian tubes by associated salpingoscopy.

FIG. 15 illustrates a first example of an examination using the multipurpose catheter 1 including a head 3 with three inlets and two channels 21 and 22.

The catheter 1 is introduced into the uterus a of a patient P in order to perform, for example, a methylene blue test so as to verify permeability of the fallopian tubes b.

The head 3, and more particularly the inlet 31, is integral with a valve 5 connected to a syringe 9 filled with a liquid comprising methylene blue, while the inlet 30 is closed tight by the head 70 of a mandrin 7.

The inlet 32 is connected via a nonreturn valve to a source of air or liquid under pressure 11 in order to inflate the balloon 40 inside the uterus a so as to obstruct the latter and seal it for introduction of the methylene blue.

The mandrins 7a or 7b are introduced via the inlet 30 which communicates with the same channel 21 as that of the inlet 31 used for introducing methylene blue so that the end 72 is accommodated in the operating site of the uterus a. The introduction of a mandrin 7a or 7b permits mobilization of the uterus a in order to facilitate its examination upon joint laparoscopy.

FIG. 16 shows another intervention using the multipurpose catheter 1 with three inlets and two channels for FERTILOSCO This operation provides for making an incision in the vaginal pouch c under local anesthetic. This FERTILOSCOPY is performed using the multipurpose catheter 1 combined with a mandrin 7 such as 7c which is introduced into the operator channel 27 of the cylindrical body 2.

The FERTILOSCOPY provides for creating an artificial ascites with serum which is injected using the multipurpose catheter into the operating site in order to permit observation of the adnexa under the most physiological conditions possible.

It is also possible, using the catheter 1 with three inlets and three routes or channels, to perform a FERTILOSCOPY by introducing surgical mandrins into the channel 27 of the cylindrical body, and in particular a clamp stabilizing the infundibulum, a FERTILOSCOPE with which it is possible to perform independent salpingoscopy.

The same channel 27 can be used to perform biopsies, hydrosalpinx incision before deciding whether to operate.

FIG. 17 shows another application of the multipurpose catheter 1 as a trocar during laparoscopy for a salpingoscopy.

The multipurpose catheter 1 is introduced into the infundibulum of a fallopian tube b which is lifted by a clamp 12. The balloon 40 is inflated by a source of air or liquid under pressure 11 which is connected to the inlet 32 via a nonreturn valve 5. A miniature endoscope 13 is introduced via the inlet 30 so that its lens is accommodated inside the infundibulum to be auscultated. This miniature endoscope is placed after the withdrawal of a mandrin 7c at end 73 making it possible to pierce the skin of the patient P.

A syringe 9 is arranged on the inlet 31 which includes another valve 5 in order to fill the infundibulum with serum, facilitating visual examination.

After withdrawing the miniature endoscope 13, salpingotomy can be performed if necessary using the balloon 40.

FIG. 18 illustrates still another application of the multipurpose catheter 1 for performing salpingoscopy. The catheter used has three inlets and three routes, so that when it has been introduced into the operating site, it is possible to move a clamp 41 through the operator channel 27, while a miniature endoscope 13 is arranged in the eccentric channel 21. The dimensions of the latter make it possible to inject a liquid around the miniature endoscope 13 during examination of the fallopian tube held by the clamp.

It will be noted that the diameters of the channels 21 and 27 are adapted to receive the rods 71 of the mandrins 7a, 7b, 7c, 7d or surgical instruments while permitting injection of a liquid in the same channel.

It will be noted that the multipurpose catheter 1, when used as a trocar, replaces the liquid infiltration sheath which is obligatory when using miniature optical endoscopes 13. In addition, the diameter of the channel 21 can receive any miniature endoscope 13 whose external diameter does not exceed 4 mm when the infiltration sheath is withdrawn.

Moreover, the cylindrical body 2 is made of a transparent plastic material permitting monitoring of the descent of the lens 13 inside the catheter 1.

It will be noted that the multipurpose catheter according to the present invention replaces the sheaths necessary when using miniature endoscopes.

Finally, it will be noted that the multipurpose catheter 1 may be most commonly used in the field of gynecology for performing all the examinations performed to date.

What is claimed is:

1. A multipurpose catheter comprising:
   a cylindrical body including a first end, a second end, and at least three internal non-coaxial channels;
   a connection mechanism disposed adjacent the first end for communicating with the at least three non-coaxial channels, the connection mechanism comprising an ergonomic monobloc head which is sealingly attached to the first end of the cylindrical body;
   the ergonomic monobloc head comprising a bulged wall having at least three independent inlets for communicating with the at least three non-coaxial channels via bores, two walls which continue from the bulged wall, and a concave inwardly curved connecting wall, the connecting wall being disposed adjacent the first end of the cylindrical body and connecting the two walls, wherein the two walls comprise first oppositely facing inclined surfaces and second oppositely facing inclined surfaces having a different inclination;
   one of the at least three internal non-coaxial channels being adapted to provide communication between at least one of the at least three independent inlets and an elastically deformable balloon disposed adjacent the second end; and
   two of the at least three internal non-coaxial channels being adapted to allow the respective introduction of a liquid and a surgical mandrin,
   wherein the ergonomic monobloc head is adapted to be gripped by a user.

2. The multipurpose catheter of claim 1, wherein the catheter is adapted for use in various medical interventions.

3. The multipurpose catheter of claim 1, wherein each of the at least three independent inlets communicates with a corresponding internal non-coaxial channel via a corresponding bore.

4. The multipurpose catheter of claim 1, wherein the catheter is adapted to simultaneously deliver the liquid and the surgical mandrin via separate internal non-coaxial channels while the balloon is expanded via a different internal non-coaxial channel.

5. The multipurpose catheter of claim 1, wherein the ergonomic monobloc head comprises an injection moldable rigid plastic material.

6. The multipurpose catheter of claim 1, wherein the first opposite facing inclined surfaces comprise a shorter length than the second opposite facing inclined surfaces and wherein each of the first and second opposite facing inclined surfaces incline inwards and towards one another.

7. The multipurpose catheter of claim 1 wherein the second end of the cylindrical body comprises a conical profile.

8. The multipurpose catheter of claim 7, wherein one of the at least three internal non-coaxial channels comprises a large main channel, the large main channel comprising an axis which corresponds to an axis of the conical profile.

9. The multipurpose catheter of claim 8, wherein the large main channel is eccentrically disposed with respect to an external diameter of the cylindrical body.

10. The multipurpose catheter of claim 1, wherein the second end comprises a cone shaped profile and wherein the balloon is fixedly disposed in an immediate proximity to the cone shaped profile.

11. The multipurpose catheter of claim 10, wherein the balloon is disposed in the immediate proximity to a widest diameter portion of the cone shaped profile.

12. The multipurpose catheter of claim 1, wherein the bores of the connection mechanism comprise separate internal bores, each of the bores providing separate sealed communication between the at least three independent inlets and the at least three internal non-coaxial channels.

13. The multipurpose catheter of claim 12, wherein the first end of the cylindrical body extends into the connection mechanism.

14. The multipurpose catheter of claim 1, wherein the catheter is adapted to introduce one of a range of surgical mandrins and a range of surgical instruments into a patient.

15. The multipurpose catheter of claim 1, wherein the connection mechanism is connected to the first end of the cylindrical body via a sealing mechanism which comprises a first ring arranged around the cylindrical body.

16. The multipurpose catheter of claim 15, wherein the first ring is disposed in a bore of the connection mechanism wherein the bore has a shoulder.

17. The multipurpose catheter of claim 16, wherein the connection mechanism further comprises a second ring arranged around the cylindrical body, the second ring being disposed in another bore of the connection mechanism.

18. The multipurpose catheter of claim 12, wherein the first and second rings are bonded to each of the cylindrical body and the connection mechanism in order to make the ergonomic monobloc head integral with the cylindrical body.

19. The multipurpose catheter of claim 15, wherein the sealing mechanism is disposed adjacent the inwardly curved connecting wall.

20. The multipurpose catheter of claim 16, wherein the connection mechanism comprises a chamber disposed in the area of the first ring and the shoulder of the bore.

21. The multipurpose catheter of claim 20, wherein the connection mechanism comprises a space which communicates with the chamber and at least one of the at least three independent inlets.

22. The multipurpose catheter of claim 1, wherein two of the at least three internal non-coaxial channels comprise different diameters, and wherein each of the two internal non-coaxial channels are offset in relation to each other.

23. The multipurpose catheter of claim 22, wherein each of the two internal non-coaxial channels are laterally offset relative to a main center axis of the cylindrical body and wherein one of the two internal non-coaxial channels communicates with two of the at least three independent inlets and wherein another channel of the two internal non-coaxial channels communicates with another of the at least three independent inlets and the balloon.

24. The multipurpose catheter of claim 1, wherein the at least three internal non-coaxial channels have different diameters which are offset in relation to each other and offset laterally in relation to a main center axis of the cylindrical body.

25. The multipurpose catheter of claim 24, wherein the at least three internal non-coaxial channels comprise a first channel, a second channel and a third channel and wherein the at least three independent inlets comprise a first inlet, a second inlet and a third inlet, wherein the first channel communicates with the first inlet, the second channel communicates with the third inlet and the balloon, and the third channel communicates with the second inlet.

26. The multipurpose catheter of claim 1, wherein the cylindrical body comprises at least one bore which cooperates with at least one bore in the connection mechanism to permit communication between at least one channel of the at least three internal non-coaxial channels and at least one inlet of the at least three independent inlets.

27. The multipurpose catheter of claim 1, wherein the cylindrical body comprises a plurality of bores which cooperate with corresponding bores in the connection mechanism to permit communication between the at least three internal non-coaxial channels and the at least three independent inlets.

28. The multipurpose catheter of claim 1, wherein the surgical mandrin comprises a head which is integral with a rod, the rod having a free end.

29. The multipurpose catheter of claim 28, wherein the free end comprises a hemispherical profile.

30. The multipurpose catheter of claim 29, wherein the rod comprises a curved profile.

31. The multipurpose catheter of claim 1, wherein the cylindrical body comprises a rigid cylindrical body.

32. The multipurpose catheter of claim 1, wherein the cylindrical body comprises a flexible cylindrical body.

33. The multipurpose catheter of claim 1, wherein the cylindrical body comprises a transparent material.

34. A multipurpose catheter comprising:
a small diameter cylindrical body including a handle end, a balloon end, and at least a first, a second, and a third internal non-coaxial channel;
a connection mechanism disposed adjacent the handle end for communicating with the first, second and third internal non-coaxial channels, the connection mechanism comprising an ergonomic handle head which is sealingly attached to the handle end;
the ergonomic handle head comprising a bulged wall having a first, a second and a third independent inlet, each of the first, second and third independent inlets communicating with a corresponding first, second, and third internal non-coaxial channel via first, second, and third bores, two walls which extend from the bulged wall, and a concave inwardly curved connecting wall, the connecting wall being disposed adjacent the handle end of the cylindrical body and connecting the two walls, wherein the two walls comprise first oppositely facing inclined surfaces and second oppositely facing inclined surfaces having a different inclination;
the first internal non-coaxial channel communicating with the first independent inlet and an elastically deformable balloon disposed adjacent the balloon end; and
the second and third internal non-coaxial channels being adapted to respectively allow introduction of a liquid and a surgical mandrin,
wherein the ergonomic handle head comprises an ergonomic shape which is adapted to be gripped by a user.

* * * * *